US008439878B2

(12) United States Patent
Bonnette et al.

(10) Patent No.: US 8,439,878 B2
(45) Date of Patent: May 14, 2013

(54) RHEOLYTIC THROMBECTOMY CATHETER WITH SELF-INFLATING PROXIMAL BALLOON WITH DRUG INFUSION CAPABILITIES

(75) Inventors: Michael J. Bonnette, Minneapolis, MN (US); Eric J. Thor, Arden Hills, MN (US); Debra M. Kozak, Forest Lake, MN (US)

(73) Assignee: Medrad, Inc., Indianola, PA (US)

( * ) Notice: Subject to any disclaimer, the term of this patent is extended or adjusted under 35 U.S.C. 154(b) by 0 days.

(21) Appl. No.: 12/338,376

(22) Filed: Dec. 18, 2008

(65) Prior Publication Data

US 2009/0171267 A1    Jul. 2, 2009

Related U.S. Application Data

(60) Provisional application No. 61/009,126, filed on Dec. 26, 2007.

(51) Int. Cl.
*A61M 5/178*    (2006.01)

(52) U.S. Cl.
USPC ............ 604/165.02; 604/167.06; 604/165.04; 604/22; 604/43

(58) Field of Classification Search ........... 604/102.01–102.03, 103.01–103.02
See application file for complete search history.

(56) References Cited

U.S. PATENT DOCUMENTS

| 3,435,826 | A | 4/1969 | Fogarty |
| 3,752,617 | A | 8/1973 | Burlis et al. |
| 3,833,003 | A | 9/1974 | Taricco |
| 3,930,505 | A | 1/1976 | Wallach |
| 4,100,246 | A | 7/1978 | Frisch |
| 4,168,709 | A | 9/1979 | Bentov |
| 4,224,943 | A | 9/1980 | Johnson et al. |
| 4,248,234 | A | 2/1981 | Assenza et al. |

(Continued)

FOREIGN PATENT DOCUMENTS

| DE | 3421390 A1 | 12/1985 |
| DE | 3705339 A1 | 9/1988 |

(Continued)

OTHER PUBLICATIONS

International Search Report from corresponding International Application PCT/US08/87422, Feb. 12, 2009.

(Continued)

*Primary Examiner* — Kevin C Sirmons
*Assistant Examiner* — Brandy C Scott
(74) *Attorney, Agent, or Firm* — David Schramm

(57) ABSTRACT

A thrombectomy catheter with a self-inflating proximal balloon having drug infusion capabilities is described. A self-inflating balloon is formed from an inflatable thin walled section of a flexible catheter tube. The self-inflating balloon includes a plurality of outflow orifices located about the peripheral circumference thereof and located proximal to an inflow gap interposed between a fluid jet emanator and the self-inflating balloon. The self-inflating balloon is inflated and expanded by internal operating pressures by proximal composite flow of fluid from the fluid jet emanator and entrained fluid from the inflow gap to uniformly space and position the outflow orifices of the self-inflating balloon in close proximity to the thrombus or vessel walls of a blood vessel. The thrombectomy catheter may be used for, among other things, thrombectomies, embolectomies, thrombus or vessel dilation, and for the delivery of drugs to a thrombus or vessel site.

8 Claims, 13 Drawing Sheets

U.S. PATENT DOCUMENTS

| | | |
|---|---|---|
| 4,290,428 A | 9/1981 | Durand et al. |
| 4,328,811 A | 5/1982 | Fogarty |
| 4,385,635 A | 5/1983 | Ruiz |
| 4,515,592 A | 5/1985 | Frankhouser |
| 4,535,757 A | 8/1985 | Webster |
| 4,610,662 A | 9/1986 | Weikl et al. |
| 4,631,052 A | 12/1986 | Kensey |
| 4,636,346 A | 1/1987 | Gold et al. |
| 4,690,672 A | 9/1987 | Veltrup |
| 4,739,768 A | 4/1988 | Engelson |
| 4,747,405 A | 5/1988 | Leckrone |
| 4,781,186 A | 11/1988 | Simpson et al. |
| 4,782,834 A | 11/1988 | Maguire et al. |
| 4,790,813 A | 12/1988 | Kensey |
| 4,834,710 A | 5/1989 | Fleck |
| 4,842,579 A | 6/1989 | Shiber |
| 4,883,459 A | 11/1989 | Calderon |
| 4,888,146 A | 12/1989 | Dandeneau |
| 4,898,574 A | 2/1990 | Uchiyama et al. |
| 4,898,591 A | 2/1990 | Jang et al. |
| 4,902,276 A | 2/1990 | Zakko |
| 4,913,698 A | 4/1990 | Ito et al. |
| 4,917,667 A | 4/1990 | Jackson |
| 4,950,238 A | 8/1990 | Sullivan |
| 5,011,469 A | 4/1991 | Buckberg et al. |
| 5,015,232 A | 5/1991 | Maglinte |
| 5,042,976 A | 8/1991 | Ishitsu et al. |
| 5,085,549 A | 2/1992 | Londry |
| 5,085,635 A | 2/1992 | Cragg |
| 5,085,649 A | 2/1992 | Flynn |
| 5,086,842 A | 2/1992 | Cholet |
| 5,090,960 A | 2/1992 | Don Michael |
| 5,092,873 A | 3/1992 | Simpson et al. |
| 5,114,399 A | 5/1992 | Kovalcheck |
| 5,135,482 A | 8/1992 | Neracher |
| 5,163,431 A | 11/1992 | Griep |
| 5,171,221 A | 12/1992 | Samson |
| 5,215,614 A | 6/1993 | Wijkamp |
| 5,221,270 A | 6/1993 | Parker |
| 5,222,941 A | 6/1993 | Don Michael |
| 5,234,416 A | 8/1993 | Macaulay et al. |
| 5,242,395 A | 9/1993 | Maglinte |
| 5,250,034 A | 10/1993 | Appling et al. |
| 5,250,059 A | 10/1993 | Andreas et al. |
| 5,254,107 A | 10/1993 | Soltesz |
| 5,259,842 A | 11/1993 | Plechinger et al. |
| 5,267,979 A | 12/1993 | Appling et al. |
| 5,273,526 A | 12/1993 | Dance et al. |
| 5,300,022 A | 4/1994 | Klapper et al. |
| 5,306,249 A | 4/1994 | Don Michael |
| 5,308,342 A | 5/1994 | Sepetka et al. |
| RE34,633 E | 6/1994 | Sos et al. |
| 5,318,518 A | 6/1994 | Plechinger et al. |
| 5,320,599 A | 6/1994 | Griep et al. |
| 5,324,285 A | 6/1994 | Cannon |
| 5,331,679 A | 7/1994 | Hirukawa |
| 5,342,386 A | 8/1994 | Trotta |
| 5,356,388 A | 10/1994 | Sepetka et al. |
| 5,358,485 A | 10/1994 | Vance et al. |
| 5,360,379 A | 11/1994 | Carelli et al. |
| 5,370,609 A | 12/1994 | Drasler et al. |
| 5,372,601 A | 12/1994 | Lary |
| 5,380,307 A | 1/1995 | Chee et al. |
| 5,385,548 A | 1/1995 | Williams et al. |
| 5,399,164 A | 3/1995 | Snoke et al. |
| 5,409,454 A | 4/1995 | Fischell et al. |
| 5,425,723 A | 6/1995 | Wang |
| 5,456,665 A | 10/1995 | Postell et al. |
| 5,456,674 A | 10/1995 | Bos et al. |
| 5,478,330 A | 12/1995 | Imran et al. |
| 5,492,532 A | 2/1996 | Ryan et al. |
| 5,496,267 A | 3/1996 | Drasler et al. |
| 5,496,294 A | 3/1996 | Hergenrother et al. |
| 5,499,973 A | 3/1996 | Saab |
| 5,513,956 A | 5/1996 | Lewis et al. |
| 5,514,092 A | 5/1996 | Forman et al. |
| 5,531,679 A | 7/1996 | Schulman et al. |
| 5,531,685 A | 7/1996 | Hemmer et al. |
| 5,536,242 A | 7/1996 | Willard et al. |
| 5,542,924 A | 8/1996 | Snoke et al. |
| 5,554,121 A | 9/1996 | Ainsworth et al. |
| 5,558,642 A | 9/1996 | Schweich, Jr. et al. |
| 5,571,094 A | 11/1996 | Sirhan |
| 5,599,299 A | 2/1997 | Weaver et al. |
| 5,599,325 A | 2/1997 | Ju et al. |
| 5,609,574 A * | 3/1997 | Kaplan et al. ................. 604/508 |
| 5,624,397 A | 4/1997 | Snoke et al. |
| 5,628,730 A | 5/1997 | Shapland et al. |
| 5,634,897 A | 6/1997 | Dance et al. |
| 5,643,279 A | 7/1997 | Trotta |
| 5,658,263 A | 8/1997 | Dang et al. |
| 5,662,608 A | 9/1997 | Imran et al. |
| 5,662,622 A | 9/1997 | Gore et al. |
| 5,668,702 A | 9/1997 | Nassimi |
| 5,676,659 A | 10/1997 | McGurk |
| 5,681,336 A | 10/1997 | Clement et al. |
| 5,683,345 A | 11/1997 | Waksman et al. |
| 5,687,714 A | 11/1997 | Kolobow et al. |
| 5,702,439 A | 12/1997 | Keith et al. |
| 5,704,926 A | 1/1998 | Sutton |
| 5,713,849 A | 2/1998 | Bosma et al. |
| 5,769,828 A | 6/1998 | Jonkman |
| 5,792,167 A | 8/1998 | Kablik et al. |
| 5,795,322 A | 8/1998 | Boudewijn |
| 5,795,325 A | 8/1998 | Valley et al. |
| 5,817,046 A | 10/1998 | Glickman |
| 5,843,022 A | 12/1998 | Willard et al. |
| 5,900,444 A | 5/1999 | Zamore |
| 5,906,590 A | 5/1999 | Hunjan et al. |
| 5,919,163 A | 7/1999 | Glickman |
| 5,928,181 A | 7/1999 | Coleman et al. |
| 5,929,633 A | 7/1999 | Fischer |
| 5,935,501 A | 8/1999 | Andrews et al. |
| 5,939,320 A | 8/1999 | Littman et al. |
| 5,944,686 A | 8/1999 | Patterson et al. |
| 5,951,513 A | 9/1999 | Miraki |
| 5,957,901 A | 9/1999 | Mottola et al. |
| 5,989,210 A | 11/1999 | Morris et al. |
| 5,989,271 A * | 11/1999 | Bonnette et al. .............. 606/159 |
| 6,001,078 A | 12/1999 | Reekers |
| 6,004,269 A | 12/1999 | Crowley |
| 6,004,339 A | 12/1999 | Wijay |
| 6,022,336 A | 2/2000 | Zadno-Azizi et al. |
| 6,024,729 A | 2/2000 | Dehdashtian et al. |
| 6,027,499 A | 2/2000 | Johnston et al. |
| 6,044,845 A | 4/2000 | Lewis |
| 6,062,623 A | 5/2000 | Lemmen |
| 6,063,069 A | 5/2000 | Cragg et al. |
| 6,068,623 A | 5/2000 | Zadno-Azizi et al. |
| 6,074,374 A | 6/2000 | Fulton |
| 6,096,001 A | 8/2000 | Drasler et al. |
| 6,099,496 A | 8/2000 | Berthiaume et al. |
| 6,106,642 A | 8/2000 | DiCarlo et al. |
| 6,129,697 A | 10/2000 | Drasler et al. |
| 6,129,698 A | 10/2000 | Beck |
| 6,135,977 A | 10/2000 | Drasler et al. |
| 6,165,199 A | 12/2000 | Barbut |
| 6,179,816 B1 | 1/2001 | Mottola et al. |
| RE37,153 E | 5/2001 | Henszey et al. |
| 6,224,570 B1 | 5/2001 | Le et al. |
| 6,241,744 B1 | 6/2001 | Imran et al. |
| 6,258,061 B1 | 7/2001 | Drasler et al. |
| 6,273,880 B1 | 8/2001 | Berg et al. |
| 6,283,950 B1 | 9/2001 | Appling |
| 6,331,176 B1 | 12/2001 | Becker et al. |
| 6,375,635 B1 | 4/2002 | Moutafis et al. |
| 6,395,208 B1 | 5/2002 | Herweck et al. |
| 6,524,300 B2 | 2/2003 | Meglin |
| 6,533,782 B2 | 3/2003 | Howell et al. |
| 6,544,220 B2 | 4/2003 | Shuman et al. |
| 6,592,549 B2 | 7/2003 | Gerdts et al. |
| 6,596,818 B1 | 7/2003 | Zamore |
| 6,652,548 B2 | 11/2003 | Evans et al. |
| 6,656,550 B1 * | 12/2003 | Zamore ........................ 428/35.7 |
| 6,676,637 B1 * | 1/2004 | Bonnette et al. ......... 604/165.02 |
| 6,749,583 B2 | 6/2004 | Briscoe et al. |
| 6,755,803 B1 | 6/2004 | Le |

| | | |
|---|---|---|
| 6,773,452 B2 | 8/2004 | Shaker |
| 6,790,196 B2 | 9/2004 | Kokate et al. |
| 6,834,842 B2 | 12/2004 | Houde |
| 6,875,193 B1 | 4/2005 | Bonnette et al. |
| 6,926,726 B2 | 8/2005 | Drasler et al. |
| 6,929,633 B2 | 8/2005 | Evans et al. |
| 6,939,320 B2 | 9/2005 | Lennox |
| 6,942,635 B2 | 9/2005 | Rosenblatt et al. |
| 6,945,951 B1 | 9/2005 | Bonnette et al. |
| 7,033,776 B2 | 4/2006 | Toombs |
| 7,131,981 B2 | 11/2006 | Appling et al. |
| 7,163,533 B2 | 1/2007 | Hobbs et al. |
| 7,182,756 B2 | 2/2007 | Saeed et al. |
| 7,220,269 B1 | 5/2007 | Ansel et al. |
| 7,226,433 B2 | 6/2007 | Bonnette et al. |
| 7,314,461 B2 | 1/2008 | Carter et al. |
| 7,374,560 B2 | 5/2008 | Ressemann et al. |
| 7,396,358 B2 | 7/2008 | Appling et al. |
| 7,399,307 B2 | 7/2008 | Evans et al. |
| 7,422,579 B2 | 9/2008 | Wahr et al. |
| 7,500,982 B2 | 3/2009 | Pepper |
| 7,726,433 B2 | 6/2010 | Satou et al. |
| 8,162,878 B2 | 4/2012 | Bonnette et al. |
| 2001/0051785 A1 | 12/2001 | Bonnette et al. |
| 2001/0051811 A1 | 12/2001 | Bonnette et al. |
| 2001/0053920 A1 | 12/2001 | Shaker |
| 2001/0056257 A1 | 12/2001 | Drasler et al. |
| 2002/0032408 A1 | 3/2002 | Parker et al. |
| 2002/0049423 A1 | 4/2002 | Howell et al. |
| 2002/0068895 A1 | 6/2002 | Beck |
| 2002/0077594 A1* | 6/2002 | Chien et al. ............... 604/103.02 |
| 2002/0120226 A1 | 8/2002 | Beck |
| 2002/0188276 A1 | 12/2002 | Evans et al. |
| 2003/0069541 A1 | 4/2003 | Gillis et al. |
| 2003/0088194 A1 | 5/2003 | Bonnette et al. |
| 2003/0139751 A1 | 7/2003 | Evans et al. |
| 2003/0195490 A1 | 10/2003 | Boatman et al. |
| 2004/0006306 A1 | 1/2004 | Evans et al. |
| 2004/0019323 A1 | 1/2004 | Carter et al. |
| 2004/0039306 A1 | 2/2004 | Eberhart et al. |
| 2004/0068248 A1 | 4/2004 | Mooney et al. |
| 2004/0093008 A1 | 5/2004 | Zamore |
| 2004/0193196 A1 | 9/2004 | Appling et al. |
| 2004/0210194 A1 | 10/2004 | Bonnette et al. |
| 2005/0049574 A1 | 3/2005 | Petrick et al. |
| 2005/0059957 A1 | 3/2005 | Campbell et al. |
| 2005/0107738 A1 | 5/2005 | Slater et al. |
| 2006/0016064 A1 | 1/2006 | Boatman et al. |
| 2006/0047239 A1 | 3/2006 | Nita et al. |
| 2006/0054123 A1 | 3/2006 | Stein et al. |
| 2006/0064123 A1 | 3/2006 | Bonnette et al. |
| 2006/0129091 A1 | 6/2006 | Bonnette et al. |
| 2006/0217791 A1 | 9/2006 | Spinka et al. |
| 2007/0010847 A1 | 1/2007 | Pepper |
| 2007/0073233 A1 | 3/2007 | Thor et al. |
| 2007/0282303 A1 | 12/2007 | Nash et al. |
| 2007/0282422 A1 | 12/2007 | Biggs et al. |
| 2008/0033350 A1 | 2/2008 | Wilson et al. |
| 2008/0188830 A1 | 8/2008 | Rosenblatt et al. |
| 2008/0275393 A1 | 11/2008 | Bonnette |
| 2008/0300576 A1 | 12/2008 | Witullo et al. |
| 2008/0306427 A1 | 12/2008 | Bailey |

FOREIGN PATENT DOCUMENTS

| | | |
|---|---|---|
| EP | 0232678 A2 | 8/1987 |
| EP | 0251512 A1 | 1/1988 |
| EP | 0528181 A1 | 2/1993 |
| EP | 1382366 A1 | 1/2004 |
| EP | 1800708 | 12/2008 |
| GB | 1571459 A | 7/1980 |
| WO | 9005493 A1 | 5/1990 |
| WO | 9410917 A1 | 5/1994 |
| WO | 9510232 A1 | 4/1995 |
| WO | WO2007067661 | 6/2007 |

OTHER PUBLICATIONS

International Search Report from corresponding International Application PCT/US08/87109, Feb. 11, 2009.

Final Rejection from corresponding U.S. Appl. No. 11/294,006, Aug. 6, 2008.

International Search Report from corresponding International Application PCT/US06/46621, Nov. 10, 2008.

ClearWay RX Product Brochure, corporate website (www.atriummed.com), Atrium Medical Corporation, as early as Oct. 2007.

Office Action Issued Mar. 17, 2009 in Corresponding U.S. Appl. No. 11/294,006.

Office Action Issued Aug. 31, 2009 in Corresponding U.S. Appl. No. 11/294,006.

Final Rejection Issued Jan. 26, 2010 in Corresponding U.S. Appl. No. 11/294,006.

Office Action from related U.S. Appl. No. 12/336,750, dated Jan. 11, 2012.

* cited by examiner

RHEOLYTIC THROMBECTOMY CATHETER WITH SELF-INFLATING PROXIMAL BALLOON WITH DRUG INFUSION CAPABILITIES

CROSS REFERENCES TO RELATED APPLICATIONS

This application claims priority from the earlier filed U.S. Provisional Application No. 61/009,126 filed Dec. 26, 2007, and is hereby incorporated into this application by reference as if fully set forth herein.

This patent application is related to patent application Ser. No. 10/455,096 filed on Jun. 5, 2003, entitled "Thrombectomy Catheter Device Having a Self-Sealing Hemostasis Valve," now U.S. Pat. No. 7,226,433.

This patent application is also related to patent application Ser. No. 11/294,006 filed on Dec. 5, 2005, entitled "Exhaust Pressure Operated Balloon Catheter System," which is pending.

This patent application is also related to patent application Ser. No. 11/096,592 filed on Apr. 1, 2005, entitled "Rapid Exchange Fluid Jet Thrombectomy Device and Method," which is pending.

BACKGROUND OF THE DISCLOSURE

1. Field of the Disclosure

The present disclosure relates to a thrombectomy catheter, but more specifically relates to a rheolytic thrombectomy catheter with a self-inflating proximal balloon having drug infusion capabilities and, for purposes of brevity, is alternately referred to herein as a rheolytic thrombectomy catheter. The terms used herein are not intended to be limited to any particular narrow interpretation unless clearly stated otherwise in this document.

2. Description of the Prior Art

Prior art and its comparison to the devices of the present disclosure are partially set forth herein. Flow cessation of prior art devices to minimize hemolysis and for other reasons has been accomplished via a balloon on a proximally placed guide catheter or by way of proprietary occlusion guidewire technology, such as, but not limited to, the use of balloons on guidewires. With respect to thrombectomy performance, prior art cross stream jet catheter designs have been described in prior patents by the present inventors or assignees. Such prior art cross stream jet catheter designs use cross stream jets flowing between outflow orifices and inflow orifices located on an exhaust tube to impinge, macerate and carry thrombus debris away from a thrombus site and through the exhaust tube. In the present disclosure, as opposed to prior art thrombectomy catheters which place outflow orifices in the exhaust tube, outflow orifices are positioned on the periphery of a self-inflated balloon to provide significantly more effective thrombus removal. For example, a peripheral cross stream jet thrombectomy catheter exhaust tube may have the diameter of 2 mm (6 Fr) and may be treating an 8 mm blood vessel. Cross stream jets flowing outwardly from the side outflow orifices are used to liberate debris such that the thrombus may be evacuated by the inflow orifices. Ideally, these side exhaust jets would typically travel outwardly at an average of 3 mm to impinge and scrub thrombus deposits on a vessel wall. If the peripheral cross stream jet thrombectomy catheter exhaust tube is off center, which is the norm, the outwardly directed side outflow cross stream jets could travel up to 6 mm to impinge and scrub thrombus on a vessel wall. The side outflow orifices are typically less than 0.66 mm in diameter and as a result the cross stream jet may travel almost 10 diameters to impinge the vessel wall. As a cross stream jet travels, the surrounding fluid slows the cross stream jet, hence, the ability to remove debris is diminished. Compare the prior scenario to the devices of the present disclosure in which the outflow orifices are located on the periphery of a self-inflating balloon. The self-inflating balloon size and catheter are selected by the physician to match the treated vessel size in order that the balloon will always inflate to attempt to be in direct contact with the thrombus. Hence, the cross stream jets will travel a very short distance (i.e., less than 10 diameters) substantially unimpeded by surrounding fluids to impinge the thrombus with maximum velocity. Secondly, inflation of the self-inflating balloon ensures centering of the device so that the vessel is treated equally in all circumferential directions. This design enables a more effective and greater removal of tougher and more organized thrombus. Furthermore, it enables a greater and more uniform delivery of drugs into this tougher mural thrombus.

Vessel safety is improved and enhanced by use of devices of the present disclosure. In previous cross flow design thrombectomy catheters, vessel damage is primarily inflicted when the vessel wall is sucked in by the negative pressures at the inflow orifices to the point that the internal high velocity jet streams can damage the vessel wall. In fact, merely moving the catheter while the inflow orifices have been sucked onto the vessel wall is a likely mechanism for vessel damage from cross stream catheters. Vessel damage increases with the size of the inflow orifices and with the proximity of the high velocity fluid jet stream origin to the inlet orifice. In the case of devices of the present disclosure, an inlet gap (inlet orifice) is positionally located away from the vessel wall by the centering action of the self-inflating balloon.

SUMMARY OF THE DISCLOSURE

The general purpose of the present disclosure is to provide a rheolytic thrombectomy catheter sold under the trademark AngioJet®, to elegantly stop and/or impede blood flow in a vessel while simultaneously increasing the efficacy of thrombus removal. Flow cessation optimizes the effectiveness of thrombectomies, embolization containment, and procedures involving drug infusion, as well as minimizing hemolysis. Other issues addressed by the use of devices of the present disclosure relate to catheter centering, thrombus and/or vessel dilation or a modified embolectomy.

The main structure and feature of devices of the present disclosure involves the use of a proximally placed self-inflating balloon integral to and formed from a thin wall section of the exhaust tube of the rheolytic thrombectomy catheter which is inflatingly deployed using the back pressure created by the operation of the high velocity fluid jet streams used in a thrombectomy catheter, such as an AngioJet® catheter. The self-inflating balloon has a plurality of outflow orifices located about its peripheral circumference. Inflation of the balloon places the outflow orifices in close proximity to the thrombus buildup on a vessel wall. High velocity fluid jet streams emitted from an emanator exit these outflow orifices as uniformly distributed cross stream jets and return through an inflow gap, substantially a large inflow orifice, the function of which is closely related to that of multiple inflow orifices.

The device is a rheolytic enhanced thrombectomy catheter and can be used for removal of thrombus in coronary arteries, peripheral arteries or veins, neurological arteries or veins, or arterial venous conduits. By sizing the balloon for the intended vessel, the expanded balloon with peripheral circumference outflow orifices will be more efficacious in removing more organized clots. The blockage of blood flow by the inflated balloon also minimizes hemolysis. Hemolysis formed from a stagnant blood field is dramatically less than that of a flowing blood field. The self-inflating balloon of the present disclosure can also be used to dilate a vascular obstruction or narrowing.

The present disclosure describes the addition of a self-inflating balloon with outflow orifices or perforations to any of the AngioJet® catheter models. The self-inflating balloon is proximally located with respect to a high velocity fluid jet stream emanator. Although balloons attached to catheters proximally or distally have been suggested in the past, this concept goes one step further by creating a self-inflating balloon out of the distal exhaust tube (Pebax® material or polyurethane, etc.) while using the exhaust pressure of the high velocity fluid jet streams to fill and sustain the self-inflating balloon for purposes of proximal protection or occlusion (and in some cases when the rheolytic thrombectomy catheter is used in an anti-grade flow, distal protection). Furthermore, the self-inflating balloon includes a plurality of outflow orifices about its peripheral circumference so that when the self-inflating balloon is inflated, the fluid outflow in the form of cross stream jets is closely and intimately directed against the thrombus. In essence, the devices of the present disclosure provide a cross stream rheolytic thrombectomy catheter where the outflow orifices are in close or intimate proximity to the vessel wall and/or thrombus. This arrangement minimizes profile, minimizes the number of components and design complexity, minimizes manufacturing costs, and is very easy to use since the self-inflating balloon is deployed automatically when the rheolytic thrombectomy catheter is activated.

Since AngioJet® catheters remove debris more effectively in a stagnant flow, this device has several applications. It could be used with a filter to more effectively remove debris from within and around the filter. Furthermore, bench testing has shown that devices of the present disclosure are substantially more efficacious at clot removal than conventional AngioJet® catheters due to a cross stream jet configuration featuring a large inflow gap (inlet orifice). Cessation of flow and the large "pocket" the self-inflating balloon creates can ultimately increase the recirculated flow rate. Devices of the present disclosure can be used just to increase the amount of debris/thrombus removed from a particular vessel length. With this in mind, it should also minimize any distal or proximal embolization. It could also be used to deliver drugs more effectively in a stagnant field. The outflow orifices in the self-inflating balloon can drive the drugs deeper into the thrombus or even treat or lavage a vessel wall. The self-inflating balloon could also be used for centering or positioning the catheter in a vessel to minimize vessel damage as described above. Hence, the inlet orifice structure, herein referred to as an inflow gap, for the rheolytic thrombectomy catheter is enlarged to enable maceration of larger and tougher embolic debris. The self-inflating balloon could slightly dilate an occluded section, an obstruction, or a narrowed area due to the pressurized outwardly directed self-inflating balloon structure, thereby providing automatic angioplasty along with debris removal. Finally, the self-inflating balloon could be used to break up clots as it is moved through a blocked vessel, thereby performing a modified embolectomy.

According to one or more embodiments of the present disclosure, there is provided a rheolytic thrombectomy catheter including a manifold, a catheter tube connected to and extending distally from the manifold, a distally located tapered flexible tip spaced distally from the distal end of the catheter tube to form an inflow gap therebetween, a tubular shaped emanator secured at the proximal end of the tapered flexible tip by the use of a marker band, a distally located thin section of the catheter tube comprising a self-inflating balloon having a plurality of outflow orifices about the peripheral circumference thereof, marker bands secured over and about the catheter tube on each end of the self-inflating balloon, and a high pressure tube extending through portions of the manifold, through the catheter tube and self-inflating balloon, and through marker bands and extending further across the inflow gap to communicatingly terminate within the emanator.

Multiple significant aspects and features of a rheolytic thrombectomy catheter incorporate and exemplify many of the features and teachings and include enhancements thereof of a rheolytic thrombectomy catheter sold under the trademark AngioJet®.

One significant aspect and feature of devices of the present disclosure is a self-inflating proximal balloon with outflow orifices, which is created from the exhaust tube itself.

One significant aspect and feature of devices of the present disclosure is a self-inflating proximal balloon with outflow orifices, which balloon is deployed by the back pressure created during operation of devices of the present disclosure.

One significant aspect and feature of devices of the present disclosure is a self-inflating proximal balloon with outflow orifices, which balloon is fixed and positioned between two marker bands with an underlying stabilizing saddle or by another suitable means.

One significant aspect and feature of devices of the present disclosure is a self-inflating proximal balloon with outflow orifices, which balloon is used for the purpose of impeding fluid flow in a blood vessel or other conduit.

One significant aspect and feature of devices of the present disclosure is a self-inflating proximal balloon with orifices, which balloon is used for the purpose of cessation of fluid flow in a blood vessel or other conduit in order to maximize the effect of a thrombectomy catheter in terms of debris or tissue removal.

Another significant aspect and feature of devices of the present disclosure is a self-inflating proximal balloon which is used for the purpose of cessation of fluid flow in a blood vessel or other conduit in order to maximize the effect of a thrombectomy catheter in terms of debris or tissue removal from a distal protection filter wire or a balloon.

One significant aspect and feature of devices of the present disclosure is a self-inflating proximal balloon used for the purpose of centering the catheter.

One significant aspect and feature of devices of the present disclosure is a self-inflating proximal balloon used for the purpose of a modified embolectomy.

One significant aspect and feature of devices of the present disclosure is a self-inflating proximal balloon used for the purpose of dilating a vessel or an occlusion.

One significant aspect and feature of devices of the present disclosure is a self-inflating proximal balloon used for the purpose of minimizing hemolysis.

One significant aspect and feature of devices of the present disclosure is a self-inflating proximal balloon used for the purpose of infusing drugs on a vessel wall or into a thrombus.

One significant aspect and feature of devices of the present disclosure is a self-inflating proximal balloon with outflow orifices used with an inflow gap for removing debris.

One significant aspect and feature of devices of the present disclosure is a self-inflating proximal balloon with outflow orifices used with one or more inflow orifices for removing debris.

Another significant aspect and feature of devices of the present disclosure is a self-inflating proximal balloon with outflow orifices used with an inflow gap or one or more inflow orifices for removing debris and used with additional radially directed spray jets emanating from a jet body loop.

Still another significant aspect and feature of devices of the present disclosure is a self-inflating proximal balloon having a diameter which could range from 2-20 mm.

Still another significant aspect and feature of devices of the present disclosure is a self-inflating proximal balloon which could range from 2-200 mm in length.

Still another significant aspect and feature of devices of the present disclosure is a self-inflating proximal balloon which could be compliant, semi-compliant, or noncompliant in nature.

Still another significant aspect and feature of devices of the present disclosure is a self-inflating proximal balloon having an internal operating pressure up to 20 ATM.

Having thus briefly described one or more embodiments of the present disclosure and having mentioned some significant aspects and features of devices of the present disclosure, it is the principal object of the present disclosure to provide a rheolytic thrombectomy catheter with a self-inflating proximal balloon with drug infusion capabilities.

BRIEF DESCRIPTION OF THE DRAWINGS

Other objects of the present disclosure and many of the attendant advantages of the devices of the present disclosure will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
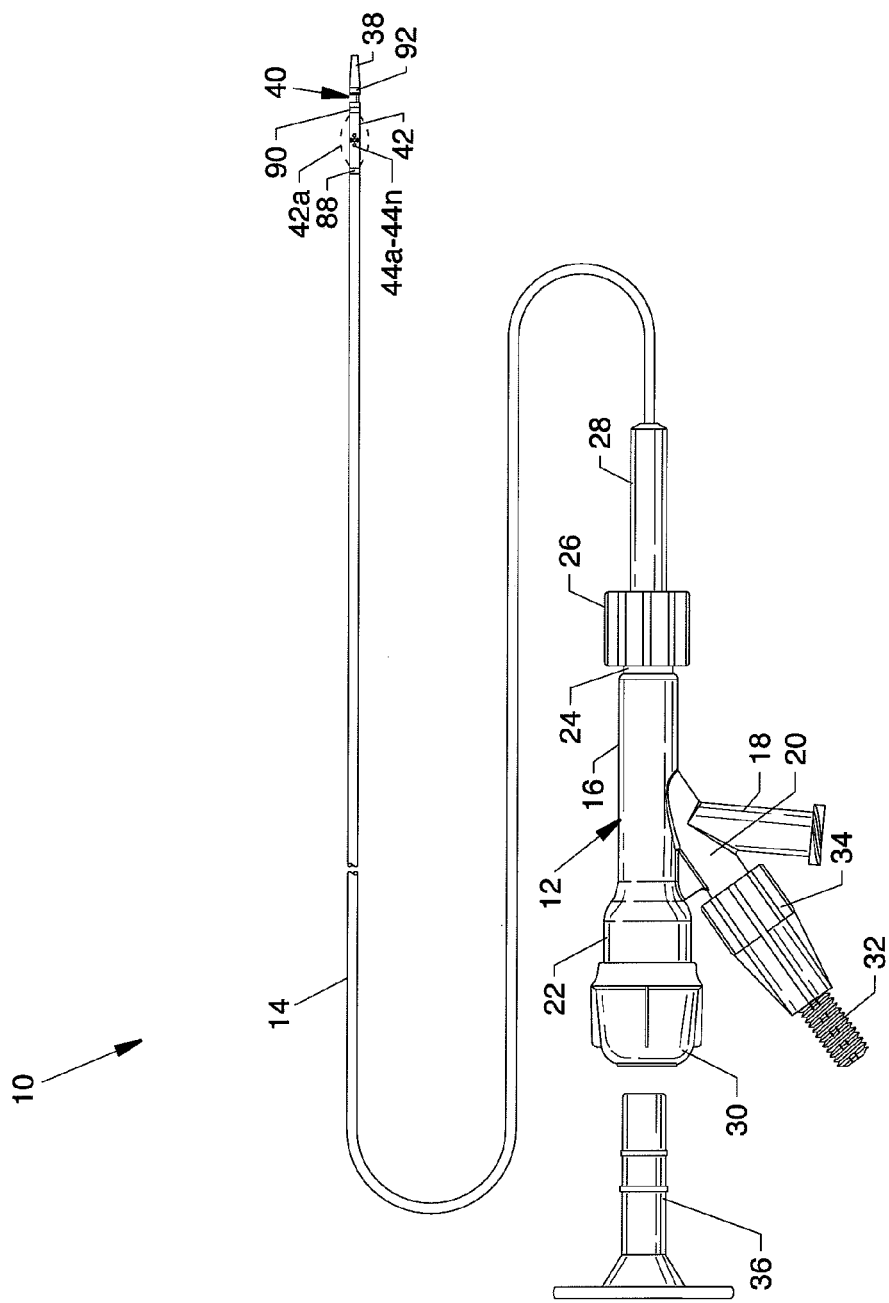
FIG. 1 is a plan view of the visible components of a rheolytic thrombectomy catheter with a self-inflating proximal balloon having drug infusion capabilities.

FIG. 1 is a plan view of the visible components of a rheolytic thrombectomy catheter 10. The device includes a one-piece manifold 12 having multiple structures extending therefrom or attached thereto, and also includes a flexible catheter tube 14 and other components associated therewith as described herein. The visible portion of one-piece manifold 12 includes a central tubular body 16, a threaded exhaust branch 18, and a high pressure connection branch 20 extending angularly from central tubular body 16, a partially shown cavity body 22 extending proximally from central tubular body 16 and a threaded connection port 24 extending distally from central tubular body 16. The proximal end of catheter tube 14 is secured to manifold 12 by the use of a Luer fitting 26 accommodated by threaded connection port 24. The proximal end of catheter tube 14 extends through a strain relief tube 28 and through Luer fitting 26 to communicate with manifold 12. Also shown is a hemostasis nut 30 aligned with and threadingly engaged with the proximal region of cavity body 22. A threaded high pressure connection port 32 is secured to high pressure connection branch 20 by a Luer connector 34. An introducer 36 is also shown.

Figure 4:
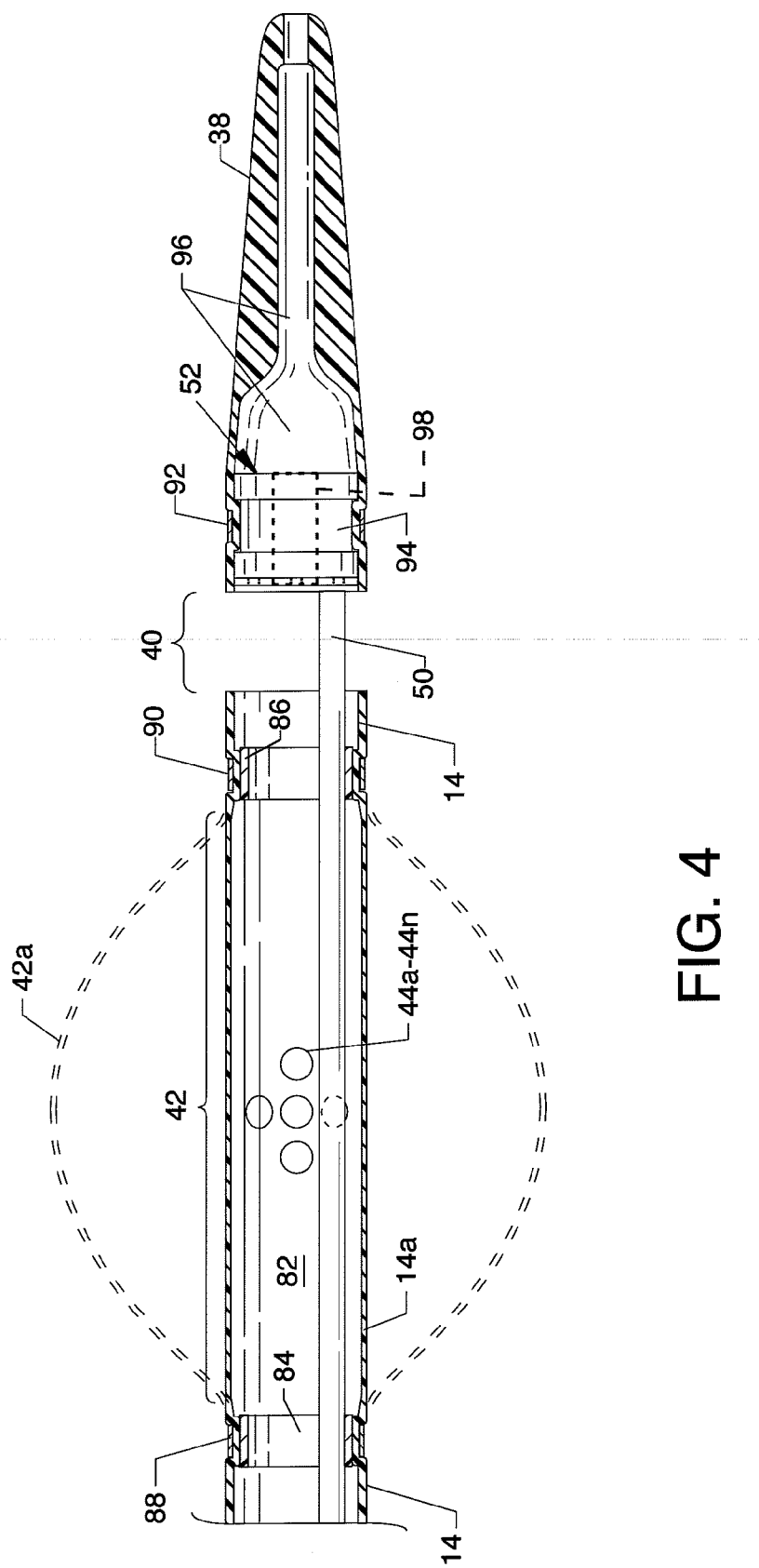
FIG. 4 is a cross section view of the distal end of the rheolytic thrombectomy catheter.
Figure 5:
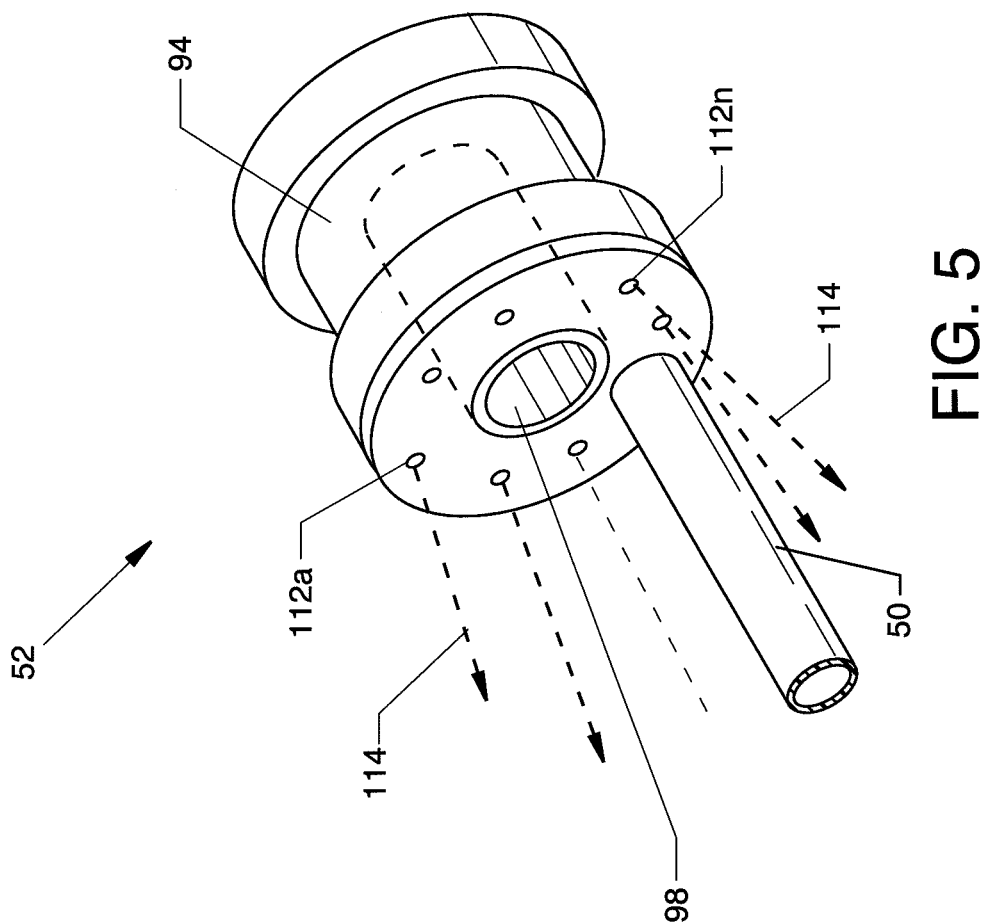
FIG. 5 is an isometric view of a fluid jet emanator having rearwardly aligned jet orifices shown connected to and in communication with a high pressure tube.

Catheter tube 14 extends distally to spacingly terminate a short distance from a tapered flexible tip 38 and a fluid jet emanator 52, not shown in FIG. 1 but shown in FIGS. 4 and 5, to provide an annular inflow gap 40. A distal section of catheter tube 14 includes a self-inflating balloon 42 (shown inflated by dashed lines 42a) proximal to inflow gap 40. A plurality of outflow orifices 44a-44n which can be arranged in various patterns is distributed about the central outer circumference of self-inflating balloon 42 for the disbursement of cross stream jets therefrom when the balloon is inflated. Catheter tube 14 functions as an exhaust tube for the evacuation of macerated effluence from the site of a thrombus or lesion. Preferably, catheter tube 14 includes a hydrophilic coating to enhance deliverability along the vasculature or other structure. Catheter tube 14 is made from a flexible plastic material or another suitable flexible material.

Figure 2:
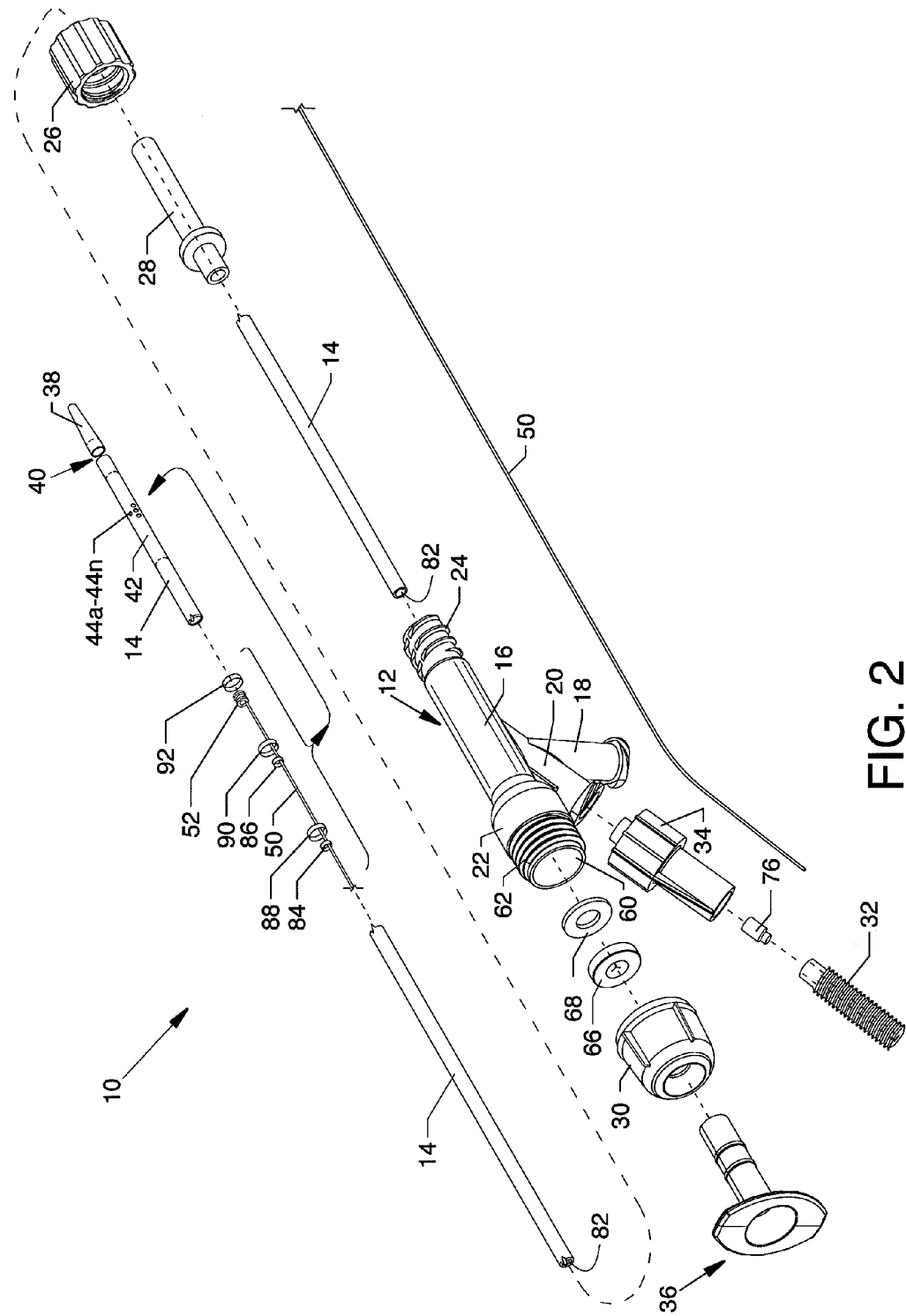
FIG. 2 is an isometric exploded and segmented view of FIG. 1 showing the rheolytic thrombectomy catheter having an inflow gap.
Figure 3:
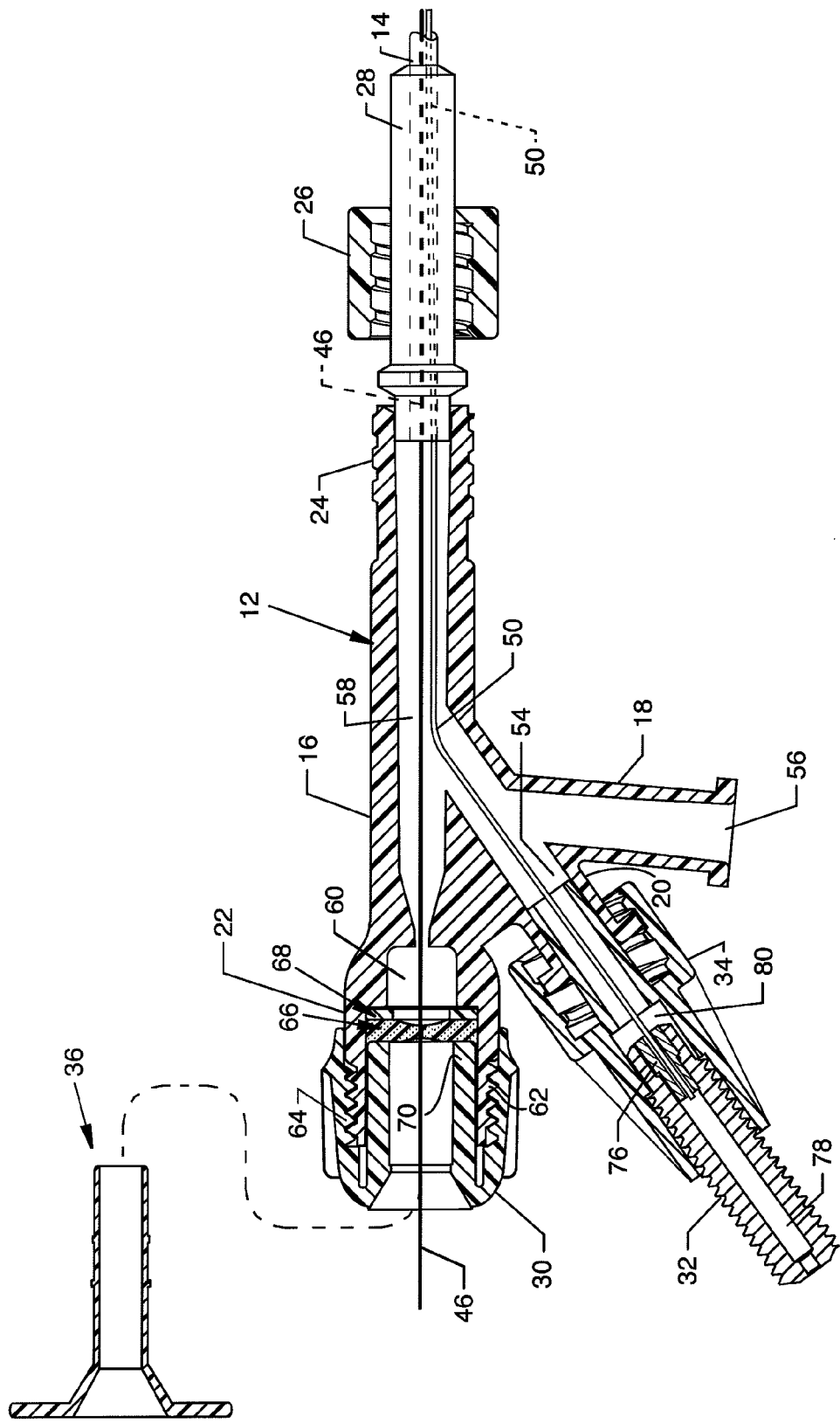
FIG. 3 is an assembled view in partial cross section of the components of the manifold shown in FIG. 2 and the closely associated components and features thereof including a guidewire.

FIG. 2 is an isometric exploded and segmented view of rheolytic thrombectomy catheter 10 and FIG. 3 is an assembled view, in partial cross section, of the components of manifold 12 and closely associated components and features thereof.

A collection of assembled components including a high pressure tube 50 and a fluid jet emanator 52 deliver a high pressure saline or other suitable fluid to the distal portion of catheter tube 14 for creation of high velocity jet streams which are directed proximally from fluid jet emanator 52 and which flow as exterior cross stream jets from the plurality of outflow orifices 44a-44n located at the peripheral circumference of self-inflating balloon 42 and return into inflow gap 40, as later described in detail. High pressure tube 50, preferably of flexible stainless steel or other suitable material, passes through and is generally distal to strain relief tube 28 and extends along a greater portion of and within a lumen of catheter tube 14 to terminate at fluid jet emanator 52. The distal end of high pressure tube 50, including fluid jet emanator 52, is also shown in greater detail in FIGS. 4 and 5.

With reference to FIGS. 2 and 3, the devices of the present disclosure are further described. Manifold 12 includes connected and communicating passageways and cavities (FIG. 3) including a high pressure connection branch passageway 54, an exhaust branch passageway 56, a tapered central passageway 58 extending from and through threaded connection port 24 and through central tubular body 16 to and communicating with a multiple radius cavity 60, which preferably is cylindrical and located central to cavity body 22. External threads 62 are located about the proximal portion of cavity body 22 at the proximal region of manifold 12 for accommodation of internal threads 64 of hemostasis nut 30.

The devices of the present disclosure benefit from the use of a flexible self-sealing hemostasis valve 66, and the use of a washer 68 which is located distal to self-sealing hemostasis valve 66, the shapes and functions of which are described in the referenced U.S. Pat. No. 7,226,433. Self-sealing hemostasis valve 66 and washer 68 are aligned in and housed in the greater radius portion of multiple radius cavity 60 of cavity body 22. Hemostasis nut 30 includes a centrally located cylindrical boss 70. Washer 68 and self-sealing hemostasis valve 66 are captured within the greater radius portion of multiple radius cavity 60 by threaded engagement of hemostasis nut 30 to threads 62 at the proximal end of manifold 12. Cylindrical boss 70 is brought to bear against the collective self-sealing hemostasis valve 66 and washer 68 to resultingly bring pressure to bear, as required, against self-sealing hemostasis valve 66, which pressure culminates in a forcible sealing of self-sealing hemostasis valve 66 about guidewire 46. Although one method of sealing against a guidewire is briefly shown and described, it is appreciated that other methods can be incorporated into this and other forms of the devices of the present disclosure such as those referenced in U.S. Pat. No. 7,226,433.

Also shown is a ferrule 76 which is aligned within a passageway 78 of threaded high pressure connection port 32, the combination of which is partially aligned within an interior passageway 80 of Luer connector 34. The proximal end of flexible high pressure tube 50, shown in segmented form in FIG. 2, can be utilized for the delivery of high pressure ablation liquids or for the delivery of drugs or other liquids and is suitably secured in a central passageway of ferrule 76 to communicate with interior passageway 78 of threaded high pressure connection port 32, as shown in FIG. 3. The proximal end of high pressure tube 50 also extends through high pressure connection branch passageway 54, through part of tapered central passageway 58, through strain relief tube 28 and Luer fitting 26, and through a lumen 82 of catheter tube 14.

High pressure tube 50 extends through support rings 84 and 86 and is suitably connected thereto, as shown in FIG. 4, to provide an anchoring and alignment structure for high pressure tube 50 in affixing the distal portion of high pressure tube 50 within the distal region of catheter tube 14. In addition, high pressure tube 50 also extends through radiopaque marker bands 88 and 90. High pressure tube 50 preferably is attached to support rings 84 and 86, such as by welding or other suitable means, where support rings 84 and 86 function as co-located supports for catheter tube 14 in the region beneath radiopaque marker bands 88 and 90. A short distal section of high pressure tube 50 extends across inflow gap 40 and terminates within an internal annular manifold (not shown) of fluid jet emanator 52, which is suitably attached thereto where fluid jet emanator 52 communicates with the lumen of high pressure tube 50, such as to a closely related fluid jet emanator described in the previously referenced patent application Ser. No. 11/096,592 or other applications or patents assigned to the assignee. Fluid jet emanator 52, also shown in FIG. 5 as an isometric view, includes an annular groove 94 which is in coordination use with a radiopaque marker band 92 to secure tapered flexible tip 38 about fluid jet emanator 52. In FIG. 2, radiopaque marker bands 88 and 90 are shown displaced a short distance distal to support rings 84 and 86 and fluid jet emanator 52 is shown displaced proximally a short distance from radiopaque marker band 92 for the purpose of clarity and are shown in frictional engagement in their actual position along and with respect to the distal portion of catheter tube 14 in FIG. 4.

The relationships of radiopaque marker bands 88, 90 and 92, support rings 84 and 86, and fluid jet emanator 52, respectively, to each other and to catheter tube 14 are shown best in FIG. 4. In FIG. 4, self-inflating balloon 42 is shown contiguous with catheter tube 14, wherein self-inflating balloon 42 has a reduced wall thickness 14a when compared to the general wall thickness of catheter tube 14. The reduced wall thickness 14a of self-inflating balloon 42 is of a suitable thickness in order to allow the inflation of self-inflating balloon 42 to thereby expand, meet and align against the wall of the vasculature or against the thrombus, whereby a thrombectomy procedure, drug delivery procedure or other procedure can take place. For the purpose of demonstration and illustration, self-inflating balloon 42 can range in length from 2 mm to 200 mm. When self-inflating balloon 42 is in the inflated state, as represented by inflated balloon 42a, the central diameter of self-inflating balloon 42 can range from 2 mm to 20 mm. Inflated balloon 42a can be expanded, as desired, with an internal pressure up to 20 ATM. Radiopaque marker bands 88 and 90 and support rings 84 and 86 are shown forcibly contacting the full wall thickness of catheter tube 14 adjacent the ends of self-inflating balloon 42, thereby allowing substantially the full length of reduced wall thickness 14a of self-inflating balloon 42 to be utilized for expansion. Expansion of self-inflating balloon 42 is shown in dashed lines by inflated balloon 42a. Alternatively, reduced wall thickness 14a of self-inflating balloon 40 can be formed from other materials, as known in the art, and then bonded or extruded to catheter tube 14 to maintain a continuous structure throughout the length of catheter tube 14.

In all embodiments of the present disclosure outflow orifices 44a-n can have any of a number of different configurations. For example, spiral or slotted cuts can be formed that extend from one end of the periphery of self-inflating balloon 42 to the other. Alternatively as few as two outflow orifices may be utilized to effectuate the delivery of fluid for thrombectomies or other procedures as described herein. Still other patterns and numbers of outflow orifices can also be utilized on all sections of the periphery of self-inflating balloon 42 without departing from the scope of the present disclosure.

Tapered flexible tip 38 is shown including a multiple radius inner passageway 96 for the accommodation of fluid jet emanator 52 and a guidewire 46 (not shown in FIG. 4). The distally located radiopaque marker band 92 is forcibly applied around the external proximal portion of tapered flexible tip 38 to cause a frictional annular engagement of the proximal portion of tapered flexible tip 38 with all or part of an annular groove 94 of fluid jet emanator 52. Such frictional engagement is sufficient to place the outer radial surface of radiopaque marker band 92 (also 88 and 90) in a position lesser than the general and greater outer radial surface of catheter tube 14, thereby providing, in part, a catheter tube 14 having no elements protruding beyond the general outer radial surface thereof for an unimpeded and smooth distal or proximal transition of catheter tube 14 within a vein, artery or the like. A passageway 98 (FIG. 5) is shown central to fluid jet emanator 52 to accommodate the passage of a guidewire.

Structure is provided to nurture and aid the introduction of and passage of the distal portion of catheter tube 14 through blood vessels, arteries and the like to the sites of thrombotic deposits or lesions. Tapered flexible tip 38, as opposed to a rounded and nontapered flexible tip, can part and more easily penetrate thrombotic deposits or lesions during its insertional travel in a distal direction instead of advancing or pushing such thrombotic deposits or lesions distally. The decreasing diameter in a distal direction of tapered flexible tip 38 also allows for an increased flexibility in negotiating and passing through tortuous paths.

Exhaust tube support rings 84 and 86 in use with radiopaque marker bands 88 and 90 in the regions surrounding the opposed ends of self-inflating balloon 42 are examples of structures offering support or reinforcement along catheter tube 14 in the regions adjacent to the ends of self-inflating balloon 42. Such support rings allow the use of a thinner wall thickness for catheter tube 14 in order to allow for a larger and more effective and efficiently sized lumen 82, as well as contributing to a reduced sized outer diameter. Such support rings also contribute to supportively maintain the diameter and overall shape of catheter tube 14 when catheter tube 14 is pushed or advanced along a vein or vessel, as well as aiding in torsional support.

FIG. 5 is an isometric view of fluid jet emanator 52 shown connected to and in communication with high pressure tube 50. Fluid jet emanator 52 includes a plurality of rearwardly aligned orifices 112a-112n paralleling the longitudinal axis of fluid jet emanator 52, as well as including the previously described annular groove 94 and passageway 98. Fluid jet emanator 52 delivers a high pressure saline or other suitable fluid to the distal portion of catheter tube 14 for the creation of high velocity jet streams 114 which are directed proximally from orifices 112a-112n of fluid jet emanator 52 and thence within the confines of self-inflating balloon 42 to contribute in the formation of inflated balloon 42a and to perform other functions as described herein. Although the use of the particular style of fluid jet emanator 52 is shown, other fluid jet emanators having other configurations, such as those disclosed in U.S. Pat. Nos. 5,370,609 and 6,676,637, both of which are incorporated herein by reference, can also be utilized with the devices of the present disclosure, along with other designs and securitization methods described in the literature by the assignee of the present disclosure. Each separate design of fluid jet emanator 52 works similarly in that they emanate high velocity jet streams 114 and can be used in lieu of the specific fluid jet emanator 52 herein disclosed; the use of other fluid jet emanators shall not be considered to be limiting to the scope of the present disclosure.

Mode of Operation

Generally, a normal guidewire is deployed in a vessel requiring treatment or, in the alternative, a filter guidewire or balloon occlusion guidewire could also be used. Distally located components of rheolytic thrombectomy catheter 10 consisting mainly of catheter tube 14, high pressure tube 50, fluid jet emanator 52, and other components directly associated therewith, are advanced over and/or along a guidewire previously positioned in the vasculature for the purpose of debris/thrombus removal, drug infusion or other procedures and maneuvered into the appropriate position for treatment. A guide catheter or sheath can be incorporated as necessary to offer assistance in placing catheter tube 14 of rheolytic thrombectomy catheter 10 within the desired location of the vasculature. Rheolytic thrombectomy catheter 10 is then activated, wherein self-inflating balloon 42 is automatically and expandingly deployed reforming as an expanded balloon 42a, and then thrombus, debris and the like are removed or drugs can be infused by a desired procedure. Self-inflating balloon 42 can be alternately pressurized and depressurized, wherein rheolytic thrombectomy catheter 10 may be moved proximally or distally during the procedure to maximize the effect of the system. When the procedure is complete, self-inflating balloon 42 is generally deflated sufficiently under normal arterial pressure to be removed safely, or deflation can be aided with a manual syringe attached to an effluent line, or deflation can be aided by means of a roller pump. Further interventions can be executed as normal over the remaining guidewire or guidewire device.

Figure 6:
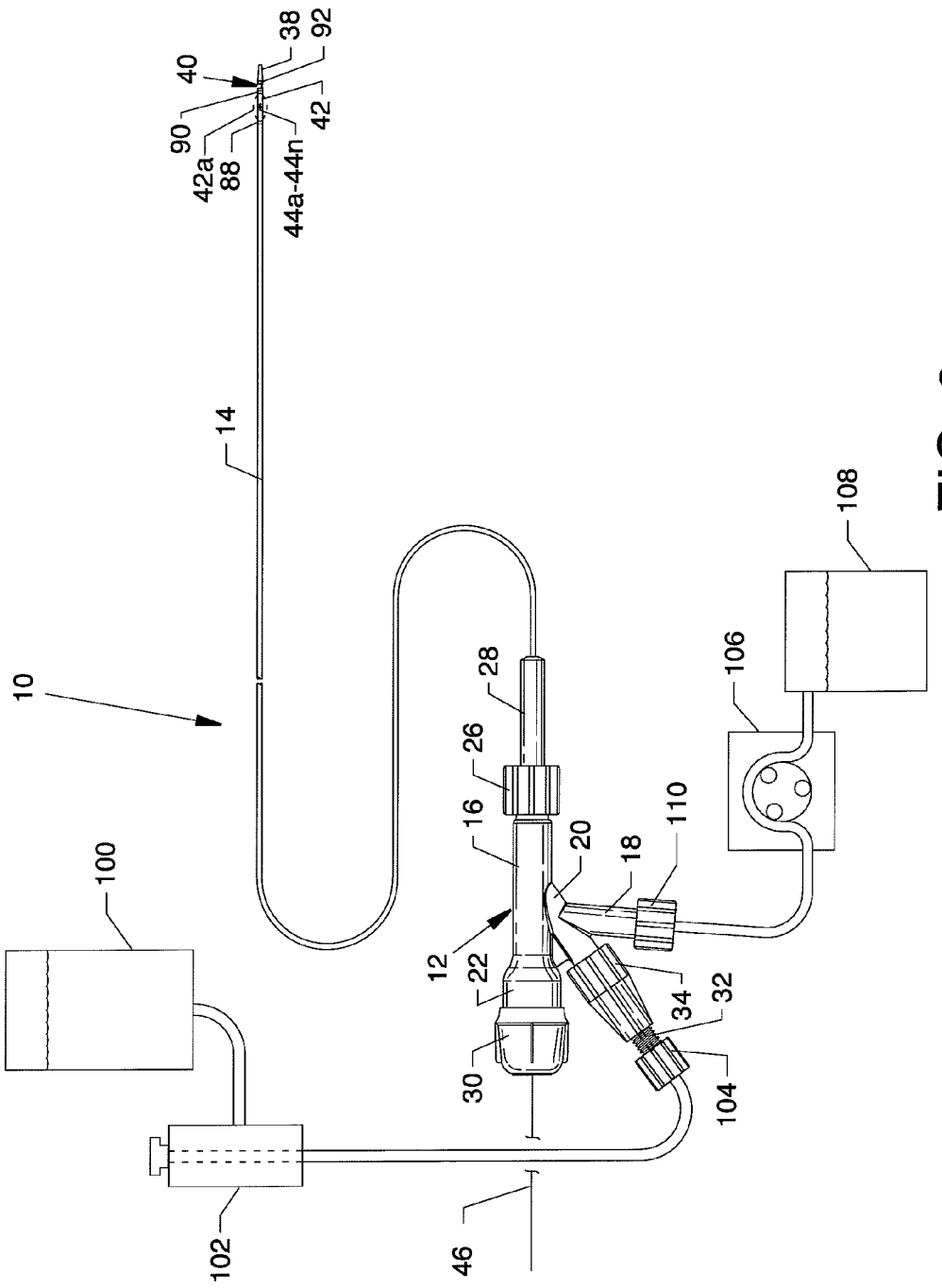
FIG. 6 illustrates the rheolytic thrombectomy catheter connected to ancillary devices.
Figure 7:
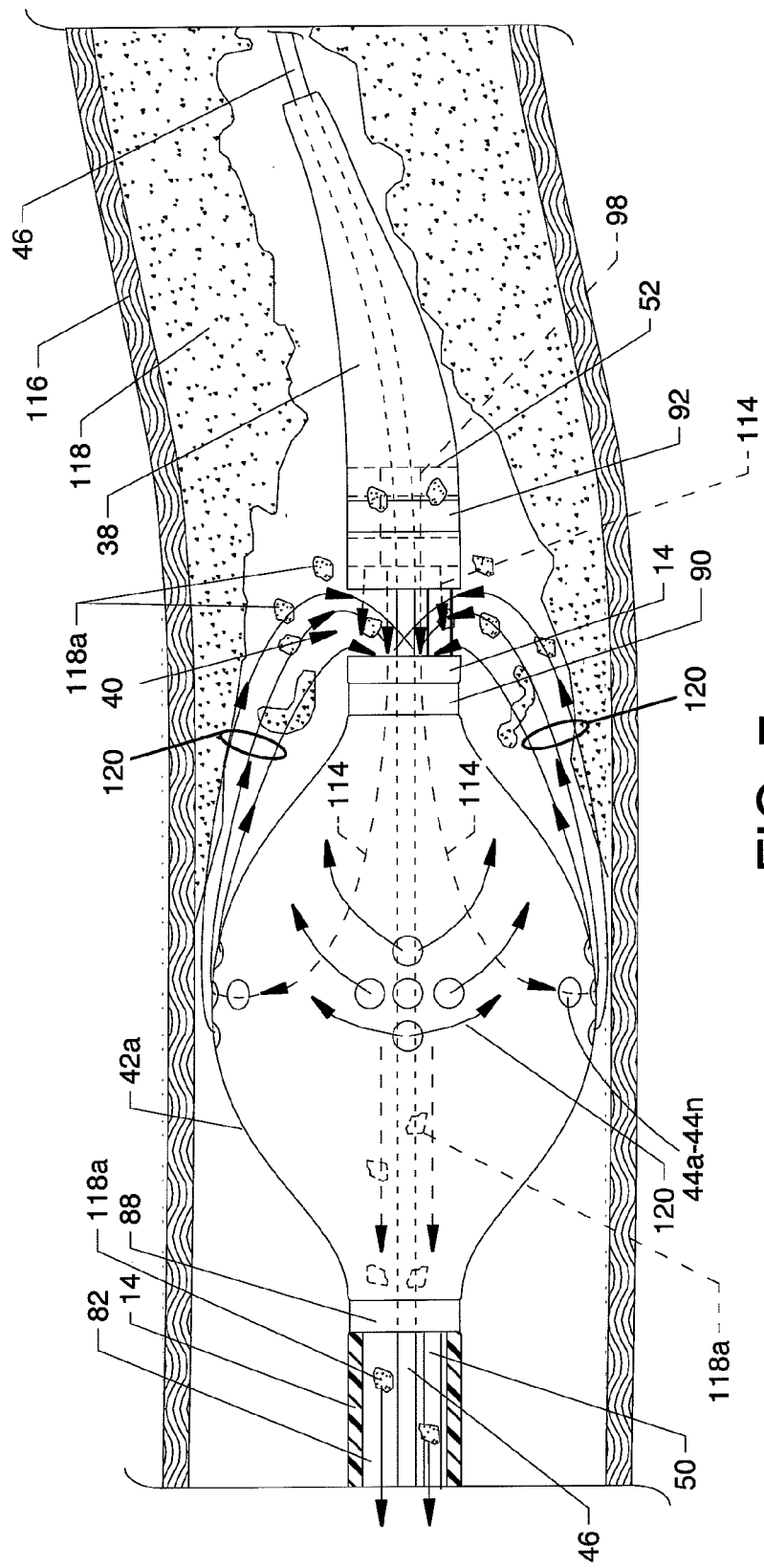
FIG. 7 is a side view in partial cross section of the distal portion of the rheolytic thrombectomy catheter.

More specifically, FIGS. 6 and 7 illustrate the mode of operation, where FIG. 6 illustrates the embodiment connected to ancillary devices, and FIG. 7 illustrates the distal portion of rheolytic thrombectomy catheter 10 in the performance of the method and use of devices of the present disclosure. The mode of operation is best understood by referring to FIGS. 6 and 7, along with the previously described figures.

In FIG. 6, rheolytic thrombectomy catheter 10 is shown engaged over and about a guidewire 46, wherein guidewire 46 (previously inserted into a vein or artery) first slidably passes through passageway 96 of tapered flexible tip 38 followed by transiting passageway 98 of fluid jet emanator 52, inflow gap 40, the distal end of lumen 82 at the distal end of catheter tube 14, self-inflating balloon 42, lumen 82 of catheter tube 14 proximal to inflow gap 40, strain relief tube 28, tapered central passageway 58, slidable within and in sealed engagement with hemostasis valve 66 and to finally exit from hemostasis nut 30. A high pressure fluid source 100 and a high pressure fluid pump 102 are connected to the manifold 12 via the threaded high pressure connection port 32 and connector 104. The fluid source may consist of saline, one or more drugs for attacking the thrombus, or a mixture of saline and one or more drugs and the fluid source can be changed dynamically while catheter tube 14 remains in the patient. An exhaust regulator 106, such as a roller pump or other suitable device, and a collection chamber 108 are connected to the threaded exhaust branch 18 by a connector 110, as shown.

FIG. 7 is a side view in partial cross section of rheolytic thrombectomy catheter 10 in the performance of the method and use thereof with particular attention given to the distal portion of catheter tube 14, flexible tapered tip 38, fluid jet emanator 52, inflow gap 40, inflated balloon 42a, and other closely associated components positioned in a blood vessel 116 at a site of a thrombotic deposit or lesion 118. Multiple high velocity fluid jet streams 114 of saline, for example, or other suitable fluid, are shown being emitted in a proximal direction from jet orifices 112a-112n of fluid jet emanator 52 in order to assist in the inflation of self-inflating balloon 42 for the purposes of, but not limited to, impeding fluid flow to effect a stagnate flow in the thrombectomy region, to provide centering of inflated balloon 42a, and to ultimately accomplish thrombectomy or drug delivery functions as described herein. Use of devices of the present disclosure can also provide for the performance of a modified embolectomy by breaking up clots as inflated balloon 42a is moved through a blocked vessel, dilating a vessel or an occlusion with inflated balloon 42a, infusing drugs on a vessel wall or into a thrombus by the use of inflated balloon 42a and outflow orifices 44a-n or to minimize any distal or proximal embolization. Self-inflating balloon 42 is pressurized by utilizing back pressure along catheter tube 14 in conjunction with the pressure of high velocity fluid jet streams 114 and is automatically and expandingly deployed reforming as an inflated balloon 42a by means of pressurized high velocity fluid jet streams 114. Inflated balloon 42a can be compliant, semi-compliant, or noncompliant according to the procedure performed. Exhaust regulator 106 is used to influence the degree of inflation of expanded balloon 42a, as well as to influence the outgoing fluidic macerated debris through catheter tube 14. Fluid jet emanator 52 or other fluid jet emanators of appropriate size and/or configuration can be incorporated within the proximal section of tapered flexible tip 38 as an alternative to emanate or emit one or more high velocity fluid jet streams 114 proximally along or near the longitudinal axis of catheter tube 14.

The positioning of the peripheral circumference of inflated balloon 42a aligns outflow orifices 44a-44n in close proximity to or against either the thrombotic deposit or lesion 118, or as generally shown in FIG. 7, in close proximity to or against the wall of blood vessel 116 in order to effect fluid flow reduction or cessation. Inflated balloon 42a substantially provides uniform centering and positioning of outflow orifices 44a-44n with respect to the surrounding thrombotic deposit or lesion 118 and/or blood vessel 116, thereby providing equally powered passage and distribution of high velocity fluid jet streams 114 outwardly from outflow orifices 44a-44n as cross stream jets 120. High velocity fluid jet streams 114 of saline pass outwardly through outflow orifices 44a-44n creating cross stream jets 120 (lower velocity jets) directed outwardly toward and for immediate contact first with the thrombotic deposit or lesion 118, if present, and thence with the wall of blood vessel 116. Cross stream jets 120 are influenced by the low pressure at inflow gap 40 to cause cross stream jets 120 to flow circumferentially and distally to impinge on, provide drag forces on, and break up thrombotic deposits or lesions 118, and to, by entrainment, urge and carry along one or more particles 118a of thrombotic deposits or lesions 118 through inflow gap 40, a relatively low pressure region, into high velocity fluid jet streams 114 where thrombus particles 118a are further macerated into microscopic particles, and then urged along lumen 82 of catheter tube 14 by the action of high velocity fluid jet streams 114. A certain portion of this macerated thrombus debris is mixed with the fresh saline high velocity fluid jet stream 114 and forcibly removed through lumen 82 of catheter tube 14 and a certain portion of this macerated thrombus flows back out outflow orifices 44a-44n and recirculates to break up more thrombus debris which is returned to inflow gap 40. In this way, much more fluid flow circulates, or recirculates, through the system, than is injected through jet orifices 112a-112n. For purposes of illustration and example, three to ten times more fluid flow circulates through the system than is delivered by jet orifices 112a-112n. The entrainment of thrombus or debris through inflow gap 40 is based on entrainment by high velocity fluid jet streams 114. The outflow of fluid and thrombus is driven proximally through catheter tube 14 by an internal pressure which is created by high velocity fluid jet streams 114 and the fluid entrained through inflow gap 40. An enhanced clot removal is attainable because of the recirculation pattern established between outflow orifices 44a-44n and inflow gap 40, which creates a flow field that maximizes a drag force on the wall-adhered thrombus. If catheter tube 14 is advanced far enough into the thrombetic deposits or lesions 118, the flow may stop when self-inflating balloon 42 inflates thereby pushing outflow orifices 44a-44n directly against the thrombetic deposits or lesions 118. When this occurs, high velocity fluid jet streams 114 drive deeply into thrombetic deposits or lesions 118 and gradually soften and then break apart the thrombetic deposits or lesions 118. Once broken, the entrained thrombus is macerated into microscopic particles and re-entrained into inflow gap 40 at a high rate. Some of the macerated particles re-exit from outflow orifices 44a-44n along with high velocity fluid jet streams 114 but are not of sufficient size to significantly block circulation. In a no-flow situation, material can then be recirculated and rediluted until all particles are removed and all that remains is saline. Cessation of fluid flow in a blood or other conduit maximizes the effect of rheolytic thrombectomy catheter 10 in terms of debris or tissue removal. Also, cessation of fluid flow in a blood vessel or other internal conduit maximizes the effect of the rheolytic thrombectomy catheter 10 when incorporated into use with a distal protection filter wire or a balloon.

Figure 8:
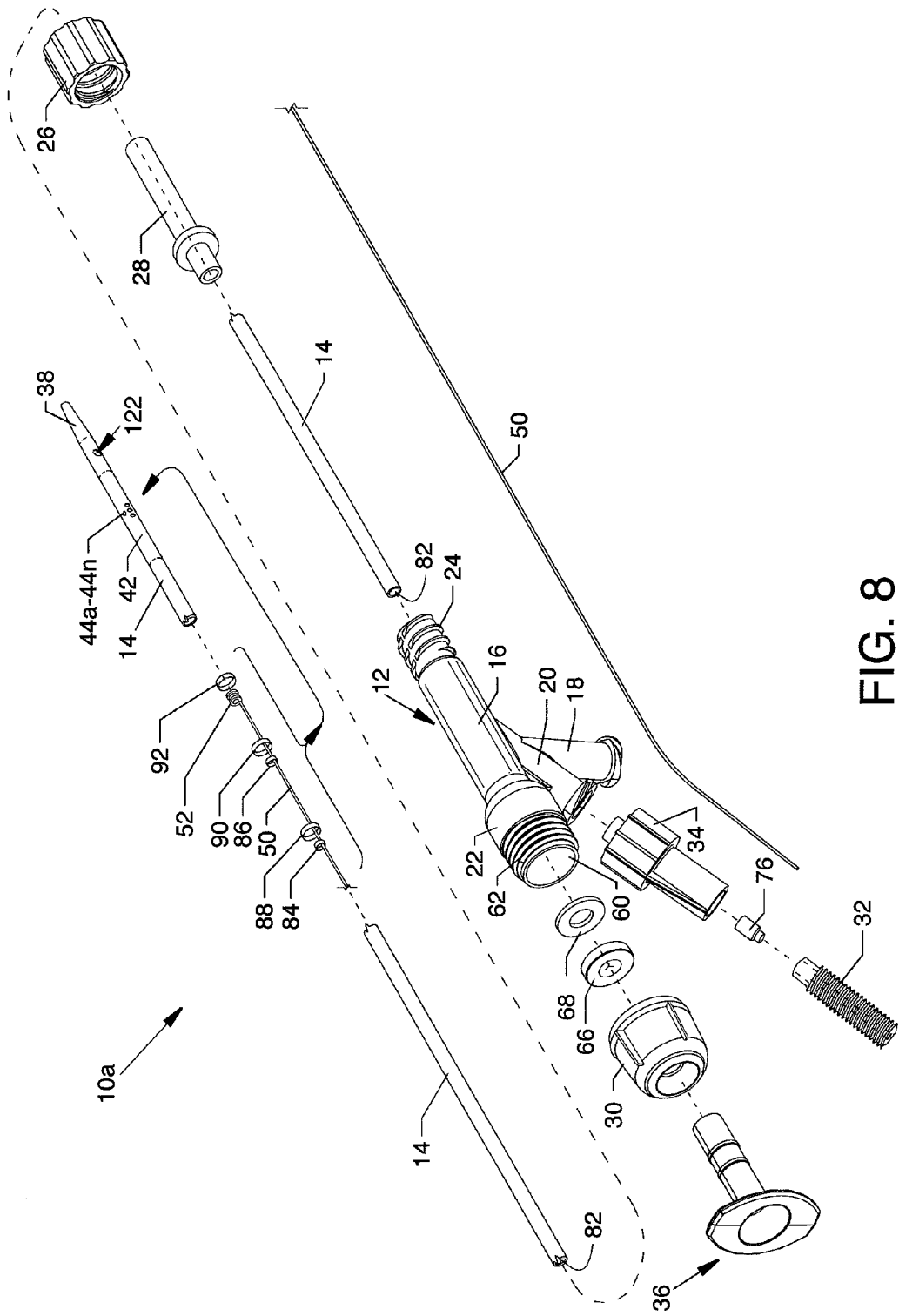
FIG. 8 is a first alternative embodiment similar to FIG. 2 illustrating a rheolytic thrombectomy catheter having a single inflow orifice.
Figure 9:
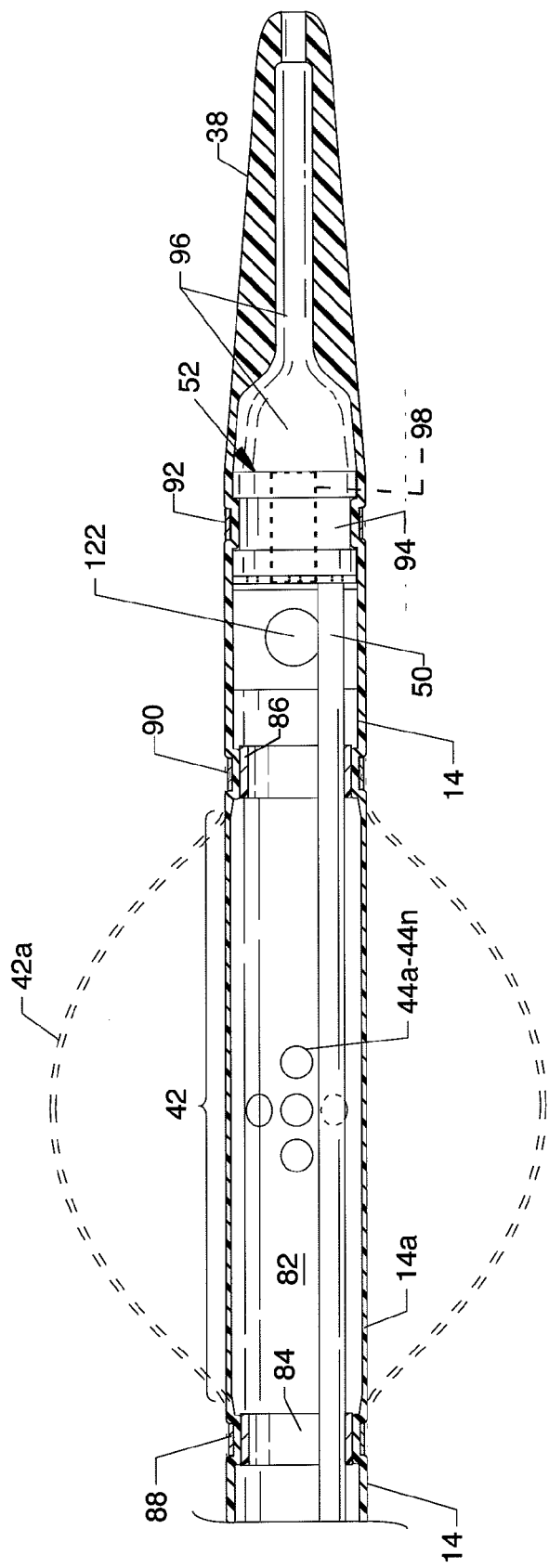
FIG. 9 is an illustration similar to FIG. 4 showing the distal end of the rheolytic thrombectomy catheter and the arrangement of the inflow orifice in relation to the self-inflating balloon.

FIG. 8, a first alternative embodiment, is an illustration similar to FIG. 2 showing a rheolytic thrombectomy catheter 10a having a single inflow orifice 122 in lieu of inflow gap 40 of the first embodiment, where all numerals correspond to those elements previously described or as otherwise described herein. In the alternative, more than one inflow orifice could be utilized instead of single orifice 122. FIG. 9 is an illustration similar to FIG. 4 showing the distal end of rheolytic thrombectomy catheter 10a and the arrangement of a single inflow orifice 122 in relation to self-inflating balloon 42. In this embodiment, catheter tube 14 extends across the former location of inflow gap 40 of the first embodiment and is continuous thereacross to form tapered flexible tip 38 in which fluid jet emanator 52 is secured in the manner previously described. The mode of operation closely parallels that of the preferred embodiment of FIG. 1, whereby inflow orifice 122, instead of inflow gap 40, is used to receive cross stream jets 120.

Figure 10:
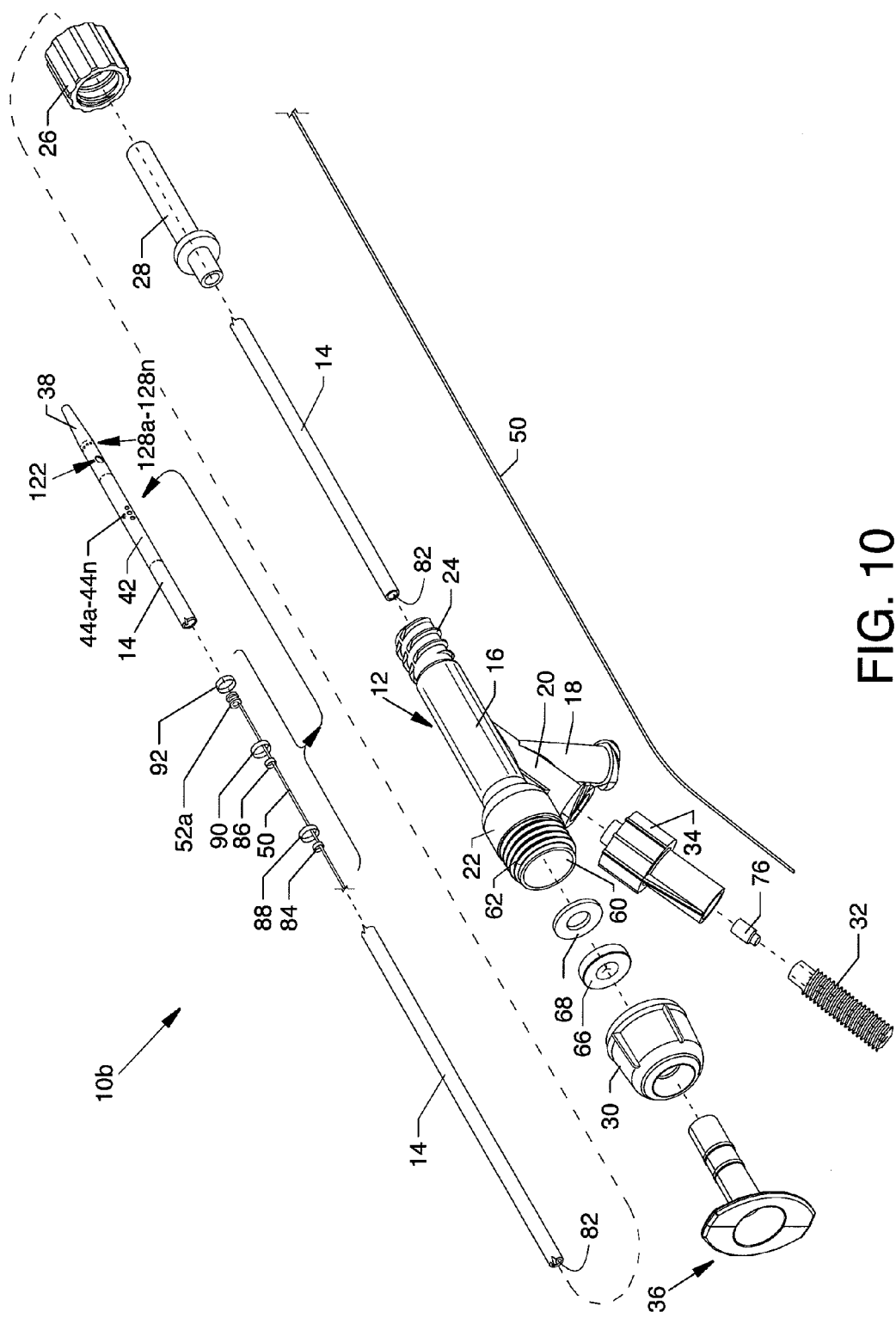
FIG. 10 is a second alternative embodiment similar to FIG. 8 illustrating a rheolytic thrombectomy catheter which can also emanate radially directed jets from the distal end thereof.

FIG. 10, a second alternative embodiment, is an illustration similar to FIG. 8 showing a rheolytic thrombectomy catheter 10b, where all numerals correspond to those elements previously described or as otherwise described herein. An additional feature of rheolytic thrombectomy catheter 10b is a fluid jet emanator 52a corresponding in general design to that of fluid jet emanator 52 shown in FIG. 11, but including features which provide for the emanation of outwardly directed high velocity fluid radial jets 124a-124n therefrom.

Figure 11:
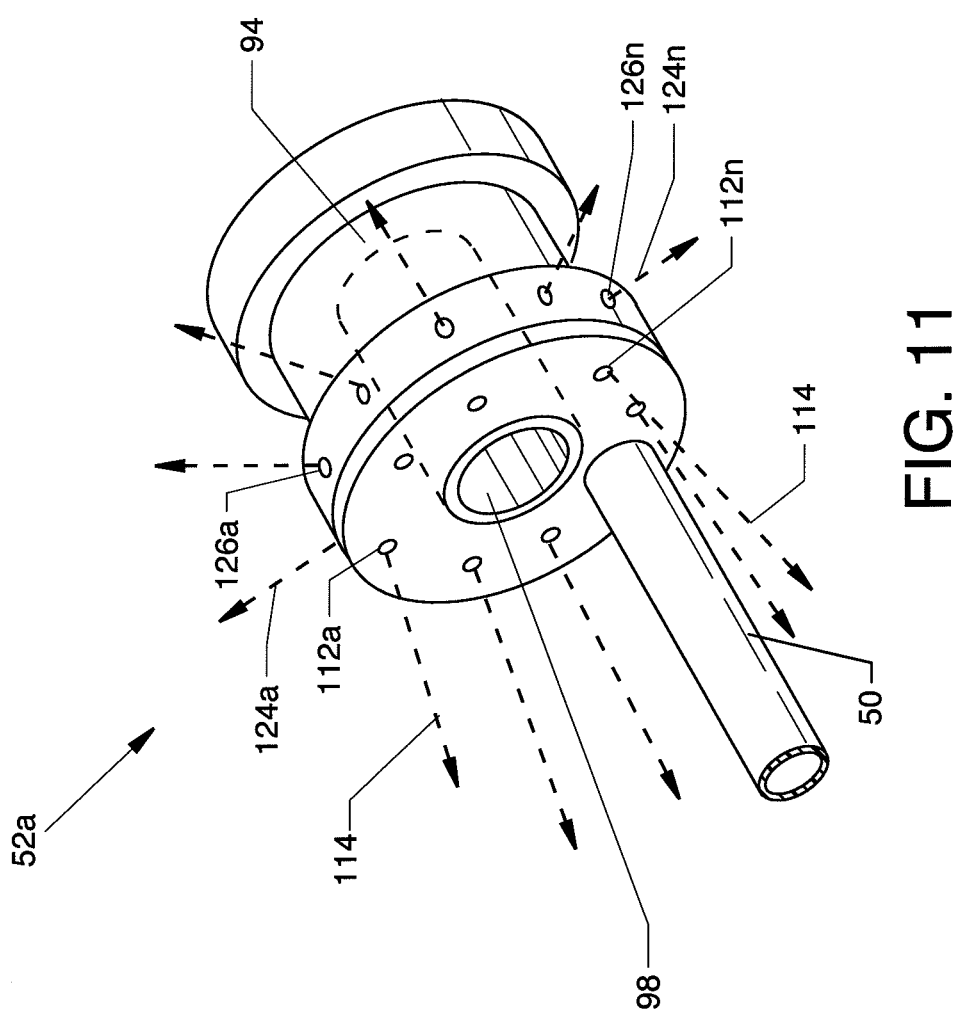
FIG. 11 is an illustration similar to FIG. 5 showing a fluid jet emanator having rearwardly aligned and radially aligned jet orifices shown connected to and in communication with a high pressure tube.

FIG. 11 is an illustration similar to FIG. 5 showing a fluid jet emanator 52a, where all numerals correspond to those elements previously described or as otherwise described herein. Additional uniformly aligned and spaced orifices 126a-126n, preferably in radial and perpendicular orientation with respect to the longitudinal axis, are arranged about a peripheral circumference of fluid jet emanator 52a and are in communication with an internal manifold (not shown) and with jet orifices 112a-112n and provide for outwardly directed emanation of high velocity fluid radial jets 124a-124n therefrom. In the alternative, the orientation of orifices 126a-126n can be randomly angulated with respect to perpendicular orientation in order to provide high velocity fluid radial jets 124a-124n at other than perpendicular emanation therefrom and directed as desired.

Figure 12:
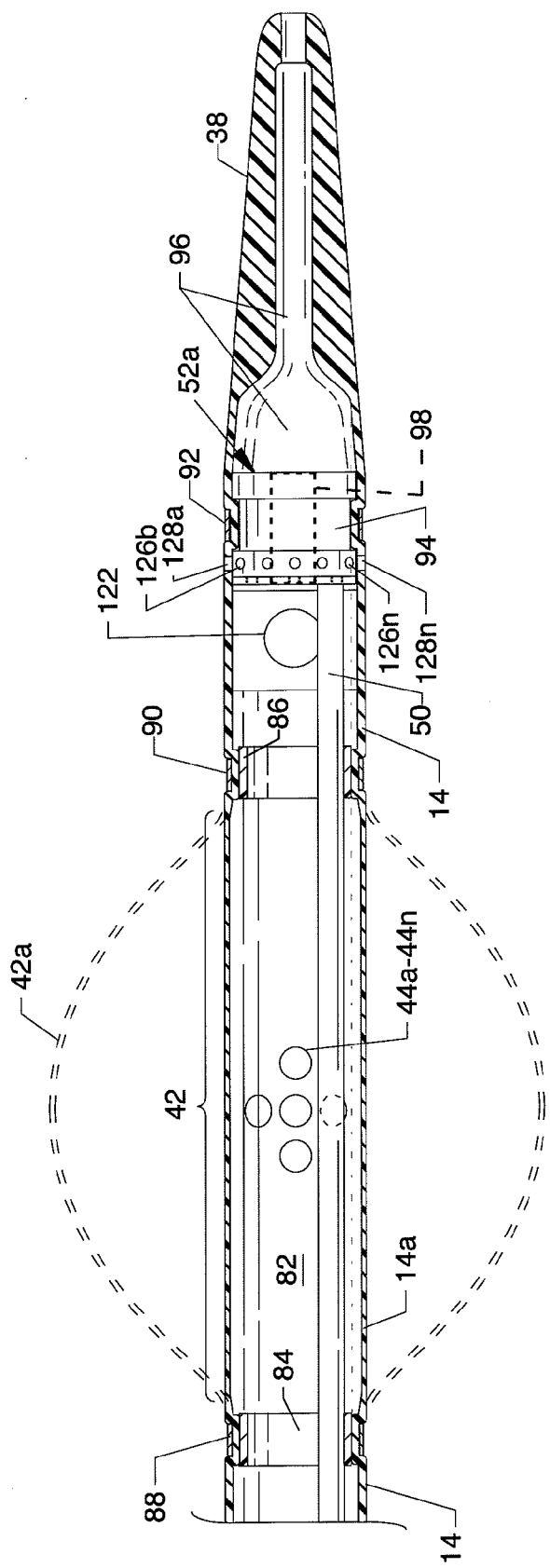
FIG. 12 is an illustration similar to FIG. 9 showing the distal end of a rheolytic thrombectomy catheter and the arrangement of the inflow orifices and the arrangement of the rearwardly and radially aligned jet orifices in relation to the self-inflating balloon; and, FIG. 13 is an illustration similar to FIG. 7 showing the performance of the method and use of the second alternative embodiment.

FIG. 12 is an illustration similar to FIG. 9 showing the distal end of rheolytic thrombectomy catheter 10b and the arrangement of an inflow orifice 122 and the arrangement of jet orifices 126a-126n of fluid jet emanator 52a in relation to self-inflating balloon 42. Also shown is the plurality of holes 128a-128n extending through the wall of the distal portion of catheter tube 14 in corresponding alignment with jet orifices 126a-126n. High velocity fluid radial jets 124a-124n (FIG. 11) emanate through the jet orifices 126a-126n and through the plurality of holes 128a-128n in order to provide treatment distal to the general flow of cross stream jets 120, as shown and described in FIG. 13.

Figure 13:
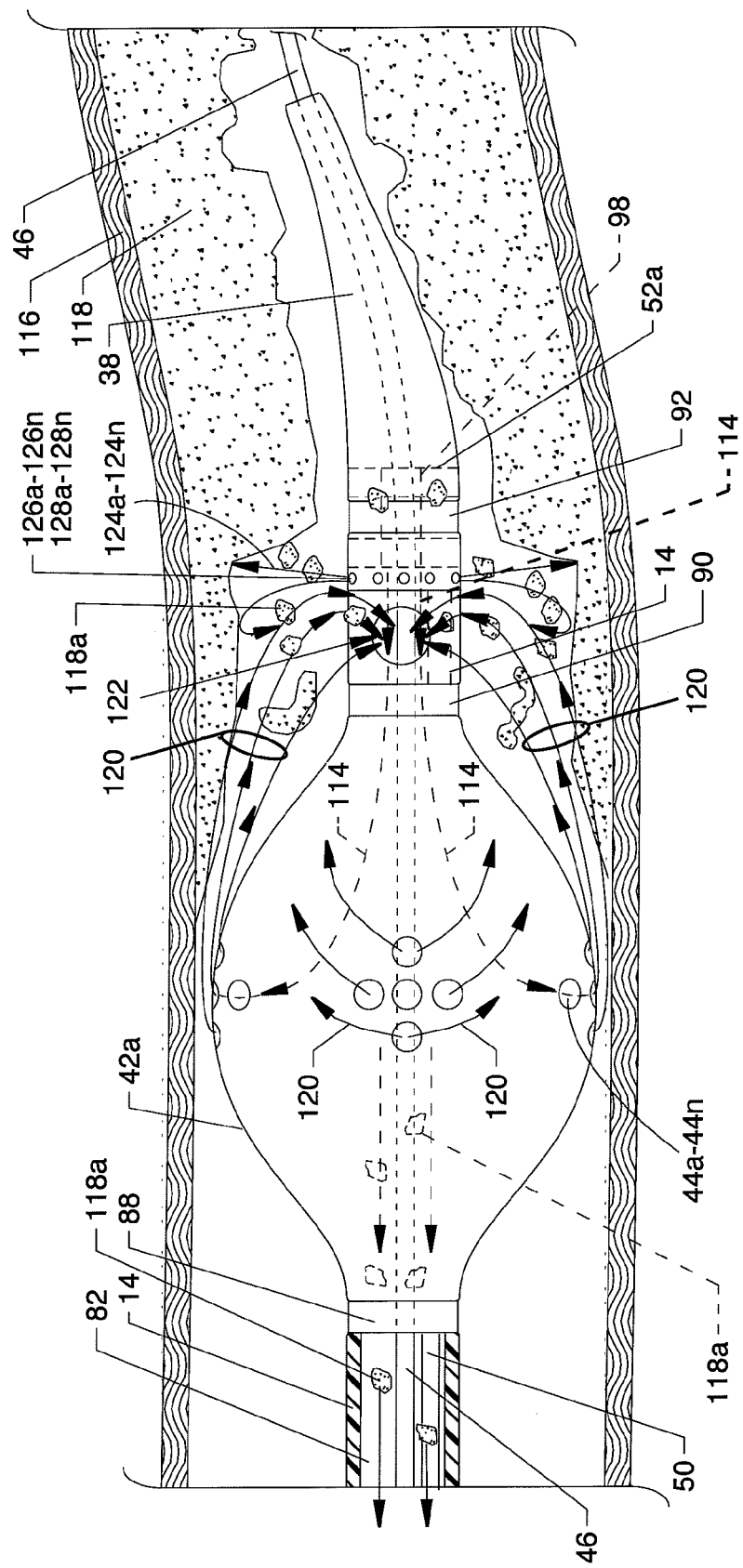

FIG. 13 is an illustration similar in operation to FIG. 7 showing flexible rheolytic thrombectomy catheter 10b in the performance of the method and use thereof. For purposes of illustration, inflow orifice 122 is oriented toward the viewer. The use of radially directed high velocity fluid radial jets 124a-124n from radial jet orifices 126a-126n provides for jet impingement of the thrombotic deposits or lesions 118 adjacent to the region of inflow orifice 122 in order to provide a substantially unrestricted path for the flow of cross stream jets 120 and particulate 118a into inflow orifice 122 for further maceration and/or carriage of fluids and particulate proximally through inflated balloon 42a and catheter tube 14 or for recirculation. Additionally, drugs for treatment or for lysing of the thrombotic deposits or lesions 118 can also be delivered via radial jet orifices 126a-126n in addition to outflow orifices 44a-n, in order to soften the thrombotic deposits or lesions 118 in the region adjacent to inflow orifice 122 and outflow orifices 44a-n, thereby benefiting and making the use of cross stream jets 120 more effective. The drugs are delivered through the high pressure tube 50 to the sites of the thrombotic deposits or lesions 118.

Various modifications can be made to the devices of the present disclosure without departing from the apparent scope thereof.

It is claimed:

1. A thrombectomy catheter comprising:
   a manifold having a central elongated tubular body with a proximal end and a distal end;
   an elongated flexible catheter tube having a proximal end and a distal end, said proximal end of said elongated flexible catheter tube extending into and distally from said distal end of said central elongated tubular body of said manifold;
   said elongated flexible catheter tube having an elongated distal section, said elongated distal section of said elongated flexible catheter tube having a proximal end and a distal end;
   said proximal end of said elongated distal section being spaced from said distal end of said elongated flexible catheter tube by an inflow gap interposed between the elongated flexible catheter tube and the elongated distal section;
   said elongated flexible catheter tube formed of a first material and further having an inflatable thin walled section adjacent to said distal end and proximal relative to the inflow gap, said inflatable thin walled section forming a self-inflating balloon in communication with the inflow gap, the inflatable thin walled section formed from the first material and having a periphery with a plurality of outflow orifices in said periphery;
   a fluid jet emanator having a plurality of spaced jet orifices, said fluid jet emanator secured within said proximal end of said elongated distal section, the inflow gap being interposed between the fluid jet emanator and the self-inflating balloon; and
   an elongated flexible high pressure tube having a proximal end in fluid communication with a fluid source and a distal end in fluid communication with the fluid jet emanator,
   wherein the self-inflating balloon is pressurized into an expanded configuration by a proximal composite flow of fluid from the fluid jet emanator and entrained fluid from the inflow gap, whereby the plurality of outflow orifices are in close proximity to a vessel wall or thrombus along the vessel wall according to the expanded configuration of the self-inflating balloon, the proximal composite flow of fluid crossing the inflow gap to the self-inflating balloon.

2. The thrombectomy catheter of claim 1, wherein said central elongated tubular body has a tubular connection branch attached thereto, a high pressure fluid connection port having a proximal end and a distal end, a high pressure fluid pump connected to said proximal end of said high pressure fluid connection port, the fluid source connected to said high pressure fluid pump and said proximal end of said elongated flexible high pressure tube in fluid communication with said distal end of said high pressure fluid connection port.

3. The thrombectomy catheter of claim 1, wherein said fluid source is selected from at least one of: saline, a solution of one or more drugs and a combination of saline and a solution of one or more drugs.

4. The thrombectomy catheter of claim 1, wherein said self-inflating balloon has an approximate length between 2 mm and 200 mm.

5. The thrombectomy catheter of claim 1, wherein said self-inflating balloon has an approximate maximum inflated diameter between 2 mm and 20 mm at a pressure up to 20 ATM.

6. The thrombectomy catheter of claim 1, wherein the plurality of outflow orifices extend from an interior of the self-inflating balloon to an exterior of the self-inflating balloon, and the proximal composite flow of fluid from the fluid jet emanator passes from the interior to the exterior of the self-inflating balloon through the outflow orifices.

7. The thrombectomy catheter of claim 1, wherein the elongated flexible high pressure tube is retained within a catheter lumen of the elongated flexible catheter tube, the inflow gap and the plurality of outflow orifices are in communication with the catheter lumen, and the proximal composite flow of fluid is directed distally through the catheter lumen to inflate the self-inflating balloon.

8. The thrombectomy catheter of claim 1, wherein the fluid jet emanator is distal relative to the inflow gap and the self-inflating balloon.

* * * * *

UNITED STATES PATENT AND TRADEMARK OFFICE
CERTIFICATE OF CORRECTION

| | | |
|---|---|---|
| PATENT NO. | : 8,439,878 B2 | Page 1 of 1 |
| APPLICATION NO. | : 12/338376 | |
| DATED | : May 14, 2013 | |
| INVENTOR(S) | : Bonnette et al. | |

It is certified that error appears in the above-identified patent and that said Letters Patent is hereby corrected as shown below:

IN THE DRAWINGS:

In Fig. 12, Drawing Sheet 12 of 13, delete "126b" and insert -- 126a --, therefor.

Signed and Sealed this
Seventeenth Day of September, 2013

Teresa Stanek Rea
*Deputy Director of the United States Patent and Trademark Office*